United States Patent
Baba

(10) Patent No.: US 6,592,252 B2
(45) Date of Patent: Jul. 15, 2003

(54) METHOD FOR MEASURING THERMAL DIFFUSIVITY AND INTERFACE THERMAL RESISTANCE

(75) Inventor: Tetsuya Baba, Tsukuba (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 0 days.

(21) Appl. No.: 09/978,003

(22) Filed: Oct. 17, 2001

(65) Prior Publication Data
US 2002/0080850 A1 Jun. 27, 2002

(30) Foreign Application Priority Data
Oct. 17, 2000 (JP) ........................................ 2000-317107

(51) Int. Cl.$^7$ ........................... G01N 25/18; G01K 11/00
(52) U.S. Cl. ............................ 374/43; 374/44; 374/161
(58) Field of Search ............................ 374/43, 44, 161

(56) References Cited

U.S. PATENT DOCUMENTS

| | | | | |
|---|---|---|---|---|
| 4,137,991 A | * | 2/1979 | Melcher et al. .............. 181/142 |
| 4,243,327 A | * | 1/1981 | Frosch et al. ................ 356/432 |
| 4,513,384 A | * | 4/1985 | Rosencwaig ................ 702/170 |
| 4,928,254 A | * | 5/1990 | Knudsen et al. ............. 702/136 |
| 5,080,495 A | * | 1/1992 | Hashimoto et al. ........... 374/43 |
| 5,112,136 A | * | 5/1992 | Sakuma et al. ................ 374/44 |
| 5,667,300 A | * | 9/1997 | Mandelis et al. ............. 374/43 |
| 5,688,049 A | * | 11/1997 | Govorkov ..................... 374/43 |

FOREIGN PATENT DOCUMENTS

| | | |
|---|---|---|
| JP | 8-261967 | 10/1996 |
| JP | 9-159631 | 6/1997 |
| JP | 10-160590 | 6/1998 |
| JP | 2001-83113 | 3/2001 |

* cited by examiner

Primary Examiner—Diego Gutierrez
Assistant Examiner—Lydia M. De Jesús
(74) Attorney, Agent, or Firm—Oblon, Spivak, McClelland, Maier & Neustadt, P.C.

(57) ABSTRACT

A non-metal film whose thermophysical properties are unknown is disposed between a first metal film and a second metal film, thereby forming a sample having a three-layer structure. The metal films have predetermined known thermophysical properties, belong to the same sort of substance and have the same thickness. The three-layer substance is disposed on a transparent substrate and is heated from below the second metal film, using a picosecond light pulse coming from below and passing through the transparent substrate. The light pulse used in the irradiation is converted into heat in the second metal film during only one picosecond, with such heat diffusing through interface/non-metal film layer/interface and thus arriving at the first metal film. By measuring a temperature change on the surface of the first metal film, it is possible to perform correct measurement by using the thermoreflectance method formerly suggested in a patent application by the inventors of the present invention.

2 Claims, 5 Drawing Sheets

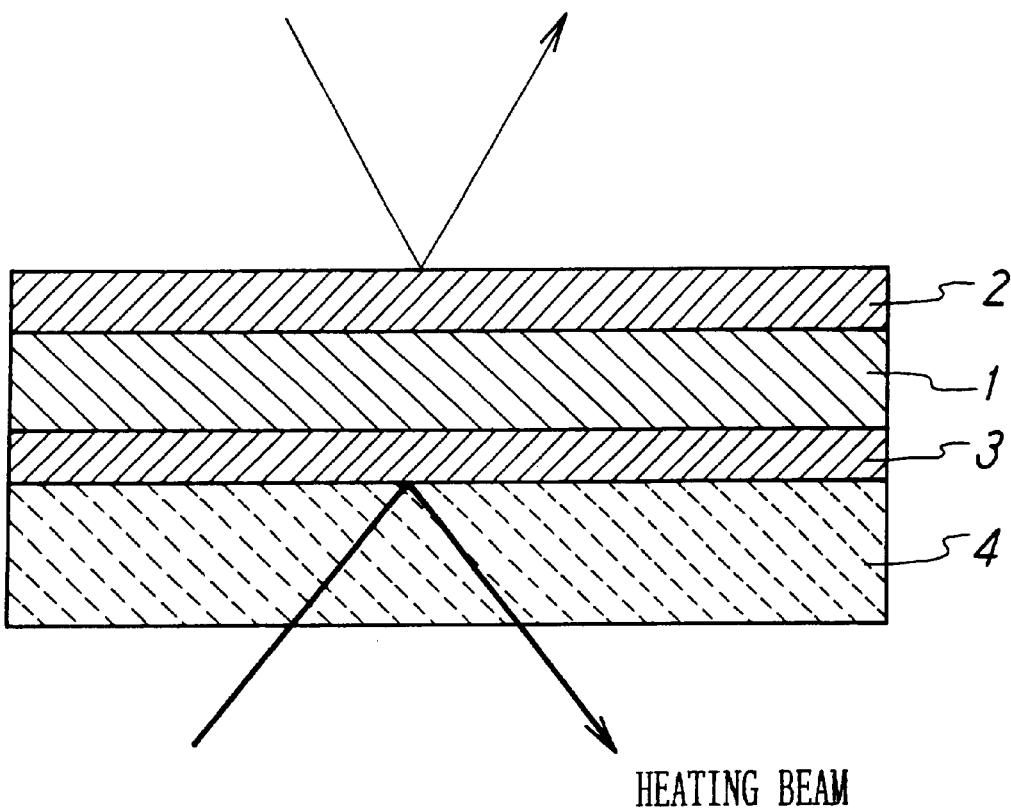

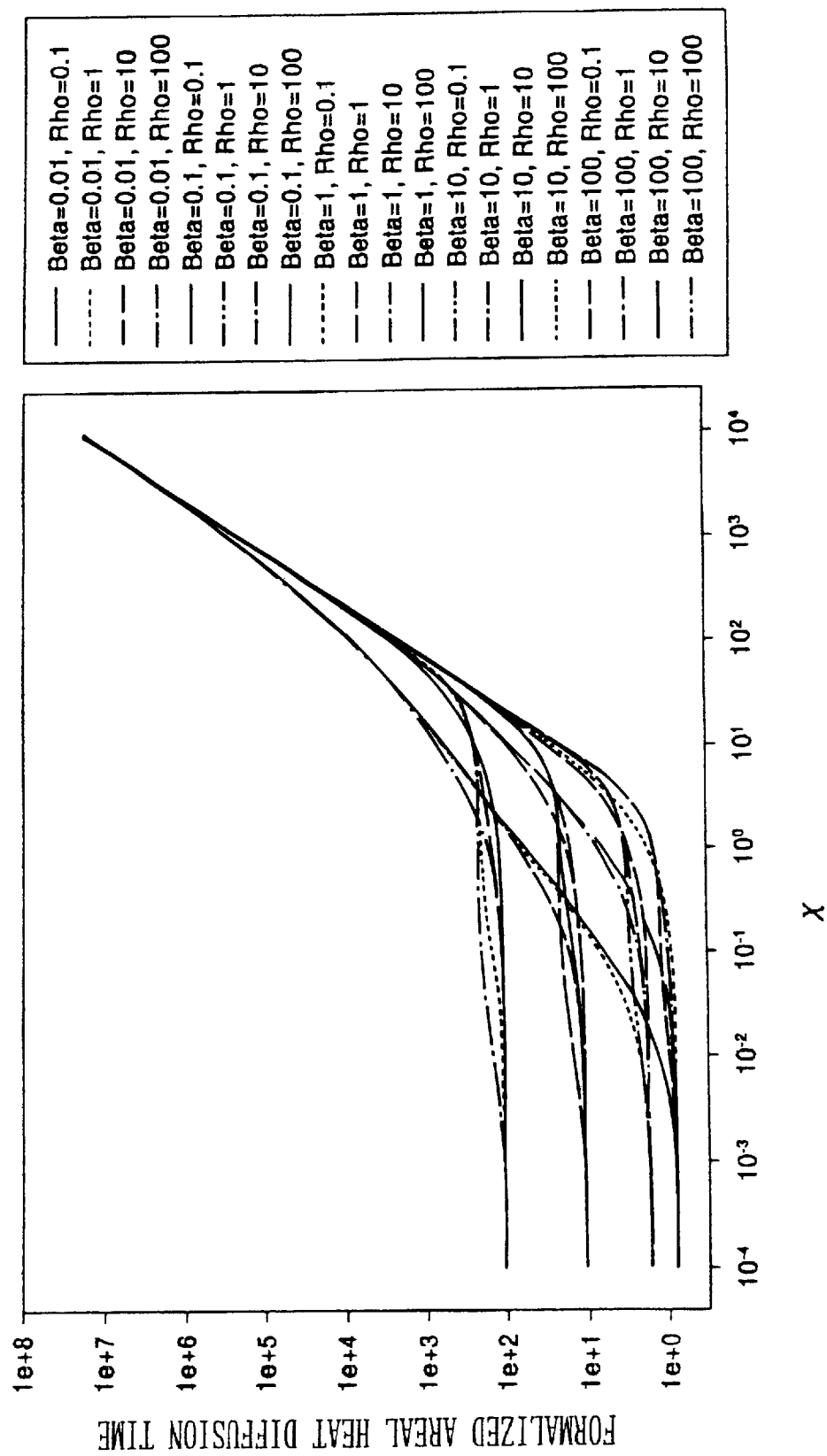

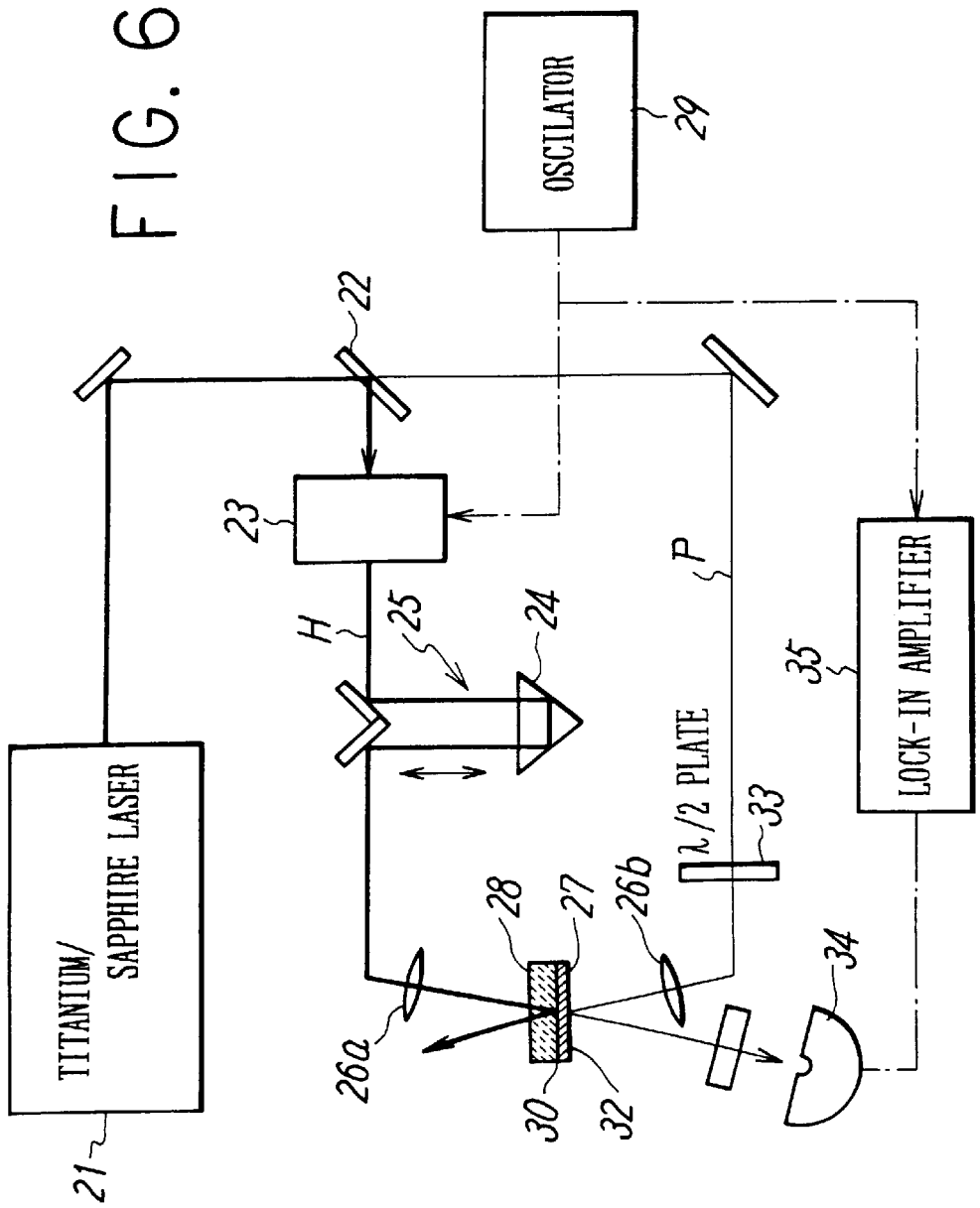

METHOD FOR MEASURING THERMAL DIFFUSIVITY AND INTERFACE THERMAL RESISTANCE

TECHNICAL FIELD OF THE INVENTION

The present invention relates to a method for measuring a thermal diffusivity within a substance having a three-layer laminated structure. In particular, this invention relates to a method for measuring a thermal diffusivity and an interface thermal resistance, which method is suitable for correctly measuring a thermal diffusivity within a three-layer film structure containing a non-metal substance, such as a semiconductor device and an optical disc type data recording medium.

DESCRIPTION OF PRIOR ART

With regard to various technical fields, thin film technique is considered to be the most advanced technique and has attracted a considerable public attention. Particularly, thin film structure plays an important role in a highly integrated semiconductor device, DVD-RAM, MO and the like. Specifically, a multi-layered thin film structure has been put into practical use, so that analyzing the properties thereof has become an important task in this field. On the other hand, although there has been a great progress in the measurement of electric, magnetic and optical properties of the above described thin film, the present situation is that there has not been a sufficient progress in the measurement of thermophysical properties of such a thin film structure. Thus, it is demanded that a rapid development take place in the field of the measurement of the thin film's thermophysical properties.

In order to fulfil the above task, the inventors of the present invention have previously developed a picosecond thermoreflectance method which involves a backside heating and a front side temperature measuring, and have been successful in measuring a thermal diffusivity in the thickness direction of a metal film having a thickness of 100 nm, as well as an interface thermal resistance between metal films. In fact, this method has already been suggested and described in Japanese Unexamined Patent Application Publication No. 2000-83113.

The basic principle of the above suggested method can be shown in FIG. 5. Namely, a metal film 10 is deposited on a transparent substrate 11. Afterwards, an interface 12 formed between the metal film 10 and the transparent substrate 11 is irradiated with a heating pulse light H so as to be heated. Meanwhile, one surface 13 of the metal film 10 is irradiated with a temperature measuring pulse light P, while a reflected light of the pulse light P is measured, thereby measuring a surface temperature of the metal film 10. In this way, it becomes possible to directly measure the thermal diffusivity of the metal film, in accordance with the metal film's thickness d which has been measured in advance, as well as a passed time period lasting from the irradiation using the heating pulse light H to the temperature measurement using the temperature measuring pulse light P.

FIG. 6 is a block diagram showing the aforementioned thermoreflectance system involving the backside heating and the front side temperature measuring, which has already been put into practical use on the base of the above discussed principle. As shown in the drawing, a light beam emitted from a titanium/sapphire laser 21 capable of generating a picosecond pulse light is splitted by a beam splitter 22, so as to be divided into two light beams, with one being a heating beam H and the other serving as a temperature measuring beam P. The heating beam H is modulated by a frequency which may be for example 1 MHz, using an acoustic optical modulator 23 controlled by an oscillator 29. The modulated heating beam H is then caused to travel through an optical delay line 25 capable of alterring a light path length by moving a prism 24.

The heating beam H having passed through the optical delay line 25 is then passed through a lens 26a so as to be focused on to an interface 30 between a metal film 27 and a transparent substrate 28. On the other hand, the temperature measuring beam P is passed through a λ/2 plate 33 and a lens 26b, so as to be focused on to the metal film's another surface 32 just opposite to the heated surface. The temperature measuring beam reflected from the surface 32 is thus detected by a silicon photo-diode 34. Meanwhile, AC component of photo-diode signal synchronized by a modulation frequency provided by the above transient thermoreflcetance oscillator 29 is detected by a lock-in amplifier 35. At this time, a signal is recorded by moving the prism 24 along the delay line 25. In fact, the above process for measuring a thermal diffusivity has been formed into a practically useful formula, and has been described in detail in a specification of a former patent application of the inventors.

On the other hand, in order to analyze the heat transfer properties of a multi-layered film structure such as a semiconductor device, DVD-ROM and MO disc, it is absolutely necessary to know not only the values of thermophysical properties of the respective layers forming the multi-layered film structure, but also the value of an interface thermal resistance existing between every two mutually adjacent film layers. However, in the case where it is required to measure an interface thermal resistance as well as a thermal diffusivity of a multi-layered film structure, the prior art method as described in the above has been proved to be extremely difficult in separately measuring a thermal diffusivity of each film layer and interface thermal resistance.

Further, with regard to a non-metal film such as a semiconductor film which is different from a metal film, in order for a laser pulse to be absorbed into the film at a depth of about 10 nm from the surface thereof, it is necessary to use a light source capable of emitting a light beam having a short wavelength. Moreover, since an absorbed light energy is usually accumulated in an excited state due to electron transition between different energy bands, a time period much longer than 1 picosecond is usually needed for arriving at a local thermal equilibrium state in which energy has been relaxed in lattice system. For this reason, the aforementioned measuring method has been found to be extremely difficult in measuring the thermal diffusivity of a non-metal thin film such as a semiconductor thin film.

SUMMARY OF THE INVENTION

An object of the present invention is to make it possible to correctly measure a thermal diffusivity of a substance even if it is a non-metal substance, also to correctly measure a thermal diffusivity within a three-layer film structure.

In more detail, the present invention is to make it possible to deal with even a non-metal substance, i.e., to simultaneously measure thermal diffusivity value as well as interface thermal resistance of the non-metal substance, by forming metal layers on both sides of the non-metal substance, using a conventional picosecond thermoreflectance method.

Further, the present invention is to make it possible to measure a thermal diffusivity within the above three-layer film substance, by preparing a plurality of substances which are different from one another only in their thicknesses and whose thermophysical properties values are unknown, and analyzing measured data about the three-layer sample, thereby making it possible to correctly measure the thermal diffusivity within the above three-layer substance.

In addition, the present invention is to make it possible to use a response function method to correctly measure the thermal diffusivity within a three-layer film structure, on the base of the above method for measuring the thermal diffusivity within the three-layer substance, in accordance with an area defined by a transient temperature history curve on the backside of the pulse-heated three-layer structure as well as the horizontal axis corresponding to a pulse-heating time.

In order to achieve the above objects, the present invention provides a method for measuring a thermal diffusivity of a three-layer substance including a middle layer whose thermophysical properties are unknown, and two other layers formed on both sides of the middle layer, said two other layers belonging to the same sort of substance and having known thermophpysical properties, characterized in that one side of the three-layer substance is heated by a pulse light, while at the same time a transient temperature history on the opposite side of the three-layer substance is observed, thereby simultaneously measuring thermophysical properties and interface thermal resistance.

Further, the above-described thermal diffusivity measuring method of the present invention is characterized in that said method comprises preparing a plurality of substances which are different from one another only in their thicknesses and whose thermophysical properties values are unknown, forming on both sides of each of the substances other substance layers which are in the same identical state and whose thermophysical properties are known, measuring the thermal diffusivity and the interface thermal resistance of each of the three-layer substances.

Moreover, the present invention is a method for measuring a thermal diffusivity of the above three-layer substance, characterized in that said method comprises calculating an area defined by a transient temperature history curve on the backside of the pulse-heated three-layer substance and a horizontal axis corresponding to a pulse-heating time, thereby simultaneously measuring thermal diffusivity within the three-layer substance as well as the interface thermal resistance.

BRIEF DESCRIPTION OF THE DRAWINGS

FIG. 1 is a cross sectional view schematically indicating the principle of the present invention.

FIG. 3 is a graph showing how an areal heat diffusion time changes, in accordance with the present invention.

FIG. 6 is a block diagram showing an apparatus for carrying out the picosecond thermoreflectance method.

DESCRIPTION OF THE EMBODIMENT

Figure 2A:
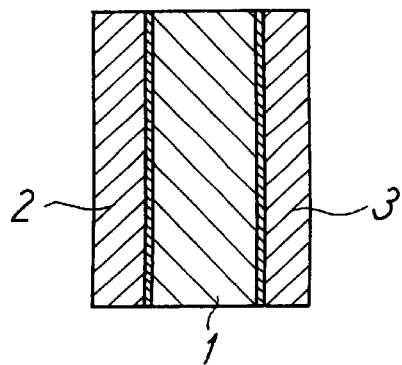
FIG. 2A and FIG. 2C are explanatory views showing two three-layer film structures used in the present invention, which contain non-metal film layers having the same identical composition but having different thicknesses.

An embodiment of the present invention will be described below in accordance with the accompanying drawings.

According to the present invention, when a thermal diffusivity of an object substance is to be measured, if the object substance is a non-metal substance such as a semiconductor, it is required to prepare a sample material in a manner as shown in FIG. 1. In detail, the sample material is a three-layer structure including a non-metal film 1 whose thermal properties are unknown, a first metal film 2 disposed on one side (an upper surface when viewed in FIG. 1) of the non-metal film 1, and a second metal film 3 disposed on the other side (a lower surface when viewed in FIG. 1) of the non-metal film 1. Here, the first and second metal films 2, 3 are the same identical substance whose thermophysical properties are known, and so formed that they have the same thickness when used in this manner. The three-layer structure is disposed on a transparent substrate 4. However, when the sample material having such a structure is to be actually formed, it is allowed to use a film formation technique to form the above film layers having predetermined thicknesses, successively on the transparent substrate 4. On the other hand, it is also possible to measure thermal diffusivity and interface thermal resistance of bulk three-layer material by a laser flash method, thereby allowing the present invention to be applied in the same manner.

Figure 5:
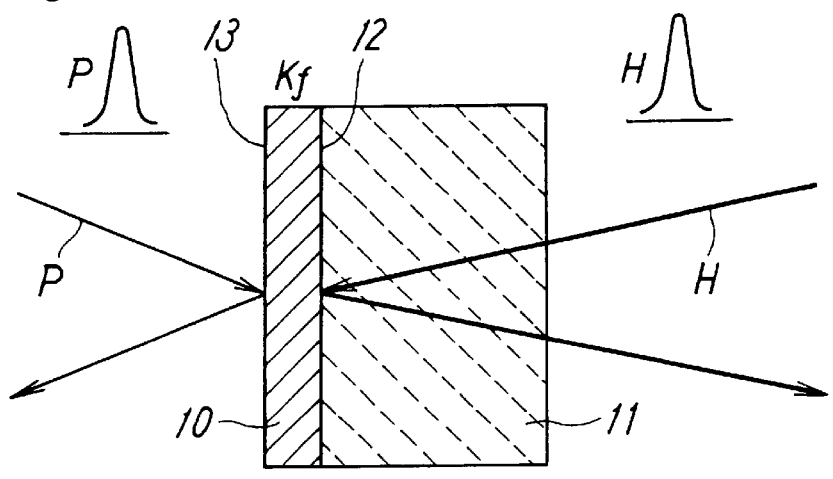
FIG. 5 is an explanatory view showing the principle of picosecond thermoreflectance method formerly suggested by the inventors of the present invention.

In this way, by using the sample material shown in FIG. 1, it is possible to employ the picosecond thermoreflectance method (involving backside heating and front side temperature measuring) formerly suggested by the inventors of the present invention, thereby making it possible to measure a thermal diffusivity within the sample material. Namely, the lower surface of the second metal film 3 is heated by virtue of an irradiation using a picosecond light pulse coming from below (when viewed in FIG. 1) and passing through the transparent substrate 4. The light pulse for use in the irradiation is converted into a heat in the second metal film 3 within only one picosecond. Such heat is then caused to diffuse through interface/non-metal film/interface, so as to arrive at the first metal film 2. In this way, if the thermoreflectance method explained in FIGS. 5 and 6 is used to measure a temperature change on the surface of the first metal film 2, it is possible to measure a heat diffusion passing through the three-layer film structure.

Figure 4A:
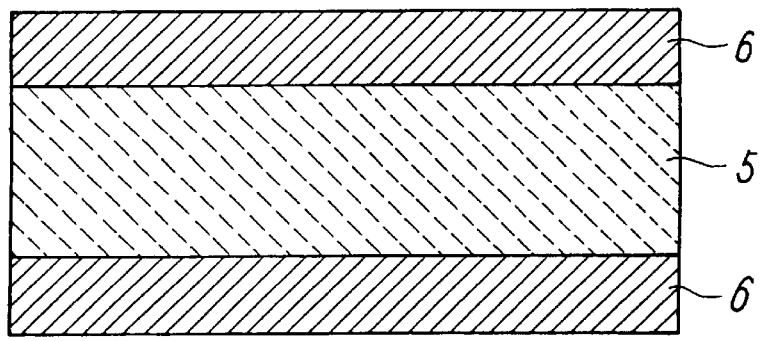
FIG. 4A and FIG. 4B are explanatory views showing three-layer structures measured by a laser flash method which is geometrically equivalent to the present invention.
Figure 4B:
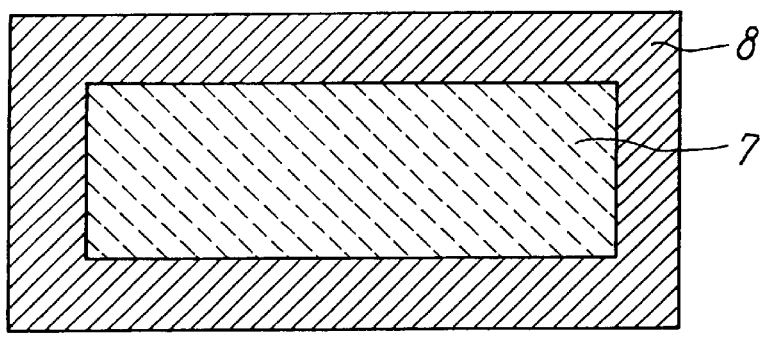

However, such an arrangement is geometrically equivalent to the case where a laser flash method is used to measure a multi-layered structure. For example, it corresponds to a situation in which a heat diffusion is measured under a condition where a transparent sample material 5 has on either side thereof a blackened thin film 6 (as shown in FIG. 4A), as well as another situation in which a heat diffusion is measured under a condition where a molten material 7 has been sealed into an opaque container 8 (as shown in FIG. 4B).

Nevertheless, with regard to the three-layer film structure shown in FIG. 1, it is not allowed to disregard the presence of interface thermal resistance between the metal films and the non-metal film, since it is not negligible as compared with the thermal resistances acting in the thickness direction of both the metal films and the non-metal film. On the other hand, when a commonly used laser flash method is employed to measure a heat diffusion within a multi-layered bulk structure, an interface thermal resistance is usually found to be much smaller than the thermal resistance of each layer.

Namely, if the picosecond thermoreflectance method formerly suggested by the inventors of the present invention is used to measure the thermal diffusivity of the three-layer film structure shown in FIG. 1, it is extremely difficult to distinguish the contribution of various film layers over the contribution of interface thermal resistance only by analyzing the sample material temperature variation graphs obtained in this method.

Figure 2B:
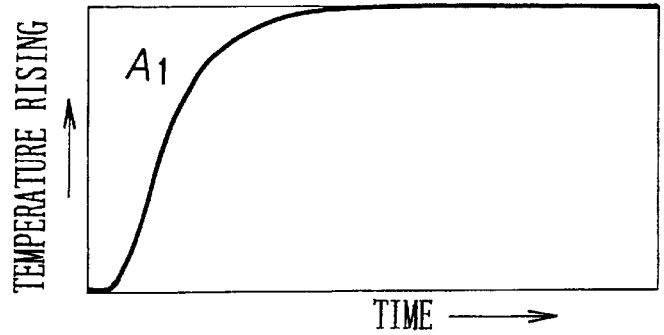
FIG. 2B.
Figure 2C:
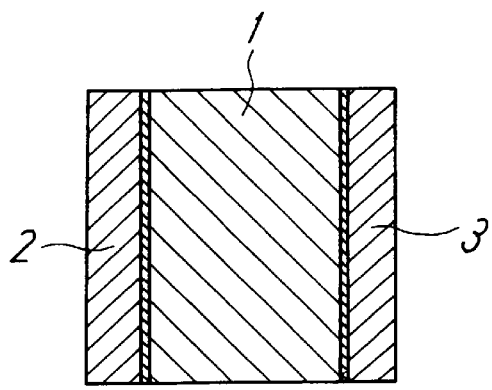

The inventors of the present invention, after carrying out various and repeated researches for solving the above problems, have found some results shown in FIG. 2A and FIG. 2C, which indicate that the above problems can be solved if the compositions of metal films 2,3 and the non-metal film 1 are completely the same as those obtainable in a film formation method, and if a plurality of three-layer film structures (only the thicknesses of their non-metal film layers 1 are different from each other) are used to carry out the above measurement.

Namely, with regard to a sample material shown in FIG. 2C (whose non-metal film layer has a relatively large thickness), its temperature rising will be later than the sample material shown in FIG. 2A. Thus, according to a view point that such a temperature change is caused by an increased heat diffusion time within a non-metal film, it is in principle possible to separately obtain a thermal diffusivity of the non-metal film and an interface thermal resistance between metal films, provided that the thermophysical properties of the non-metal film are known. In practice, it is allowed to use a response function method to obtain the above thermal diffusivity and the interface thermal resistance, thereby rendering the method of the present invention more concrete.

Figure 2D:
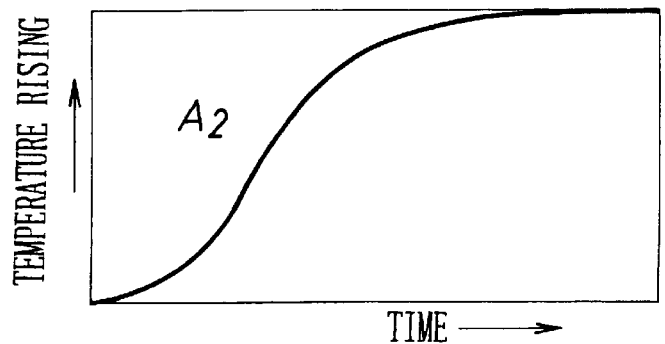
FIG. 2D are explanatory views showing areal heat diffusion times, on the sample materials of FIG. 2A and FIG. 2C.

According to the response function method, an area A defined by a sample material backside temperature history curve (after pulse heating) and a straight line of maximum temperature rising may be calculated by the following equation (1). In fact, such an area has a time dimension and can also be referred to as "areal heat diffusion time". Here, $A_1$ in FIG. 2B and $A_2$ in FIG. 2D are areal heat diffusion times corresponding to the respective sample materials.

The meanings of various marks used in the following equations are as follows.

NOMENCLATURE $\tilde{\xi}$: Laplace parameter
$\tilde{T}(\xi)$: Laplace transform of temperature
$\tilde{S}(\xi)$: Four-pole matrix
d: Thickness
α: Thermal diffusivity
b: Thermal effusivity
$\tau = d^2/\alpha$: Heat diffusion time across the film
A: Areal heat diffusion time
R: Interface thermal resistance $$\beta = b_n/b_m,\ \chi = \sqrt{\tau_n}\ /\sqrt{\tau_m},\ \rho = \frac{Rb_m}{\tau_m^{1/2}}$$

Subscripts
i: i-th layer (i=1: heated face)
ij: boundary between i-th layer and j-th layer
m: metal, n: nonmetal $$A = \int_0^\infty \left[1 - b\sqrt{\tau} \cdot T(t)\right]dt = \lim_{\xi \to 0}\left[\frac{1}{\xi} - b\sqrt{\tau} \cdot \tilde{T}(\xi)\right] \quad (1)$$

When deriving an analytical solution of the three-layer film structure's sample temperature change associated with an interface thermal resistance as shown in FIG. 2, an effect of heat effusion into the substrate is disregard and it is assumed that the three-layer film structure is thermally insulated from the surrounding environment. Further, it is assumed that the heating treatment using the laser pulse as well as the temperature measurement using the thermoreflectance are all carried out on an infinitely thin flat plane and that the heat diffusion is only one-dimensional heat diffusion in the thickness direction. At this time, a four-terminal matrix for the three-layer film structure may be expressed in the following equation.

$$\tilde{S}(\xi) = \begin{bmatrix} \cosh\sqrt{\xi\tau_3} & -b_3\sqrt{\xi}\cdot\sinh\sqrt{\xi\tau_3} \\ -\frac{1}{b_3\sqrt{\xi}}\cdot\sinh\sqrt{\xi\tau_3} & \cosh\sqrt{\xi\tau_3} \end{bmatrix} \quad (2)$$

$$\begin{bmatrix} 1 & 0 \\ -R_{23} & 1 \end{bmatrix}\begin{bmatrix} \cosh\sqrt{\xi\tau_2} & -b_2\sqrt{\xi}\cdot\sinh\sqrt{\xi\tau_2} \\ -\frac{1}{b_2\sqrt{\xi}}\cdot\sinh\sqrt{\xi\tau_2} & \cosh\sqrt{\xi\tau_2} \end{bmatrix}.$$

$$\begin{bmatrix} 1 & 0 \\ -R_{12} & 1 \end{bmatrix}\begin{bmatrix} \cosh\sqrt{\xi\tau_1} & -b_1\sqrt{\xi}\cdot\sinh\sqrt{\xi\tau_1} \\ -\frac{1}{b_1\sqrt{\xi}}\cdot\sinh\sqrt{\xi\tau_1} & \cosh\sqrt{\xi\tau_1} \end{bmatrix}$$

If the four-terminal matrix is calculated and then converted into a transfer function matrix, further, if the sample material temperature change in Laplace space is calculated and then used to substitute in the above equation (1), as well as an areal heat diffusion time is calculated, it is allowed to obtain the following equation.

$$A_{3b} = \lim_{\xi \to 0}\left[\frac{1}{\xi} - (b_1\sqrt{\tau_1} + b_2\sqrt{\tau_2} + b_3\sqrt{\tau_3})\cdot\tilde{T}(\xi)\right] \quad (3)$$

$$= A_3 + \frac{\left[\begin{array}{c}R_{12}b_1b_2\tau_1^{1/2}\tau_2^{1/2} + R_{23}b_2b_3\tau_2^{1/2}\tau_3^{1/2} + \\ (R_{12} + R_{23})b_1b_3\tau_1^{1/2}\tau_3^{1/2}\end{array}\right]}{b_1\sqrt{\tau_1} + b_2\sqrt{\tau_2} + b_3\sqrt{\tau_3}}$$

Here, $A_3$ is the three-layer film structure's areal heat diffusion time when an interface thermal resistance is 0, and can be represented by the following equation.

$$A_3 = \frac{\left[\begin{array}{c}b_1\sqrt{\tau_1}\left(\frac{\tau_1}{6} + \frac{\tau_2}{2} + \frac{\tau_3}{2}\right) + b_2\sqrt{\tau_2}\left(\frac{\tau_1}{2} + \frac{\tau_2}{6} + \frac{\tau_3}{2}\right) + \\ b_3\sqrt{\tau_3}\left(\frac{\tau_1}{2} + \frac{\tau_2}{2} + \frac{\tau_3}{6}\right) + \frac{b_1b_3}{b_2}\tau_1^{1/2}\tau_2^{1/2}\tau_3^{1/2}\end{array}\right]}{b_1\sqrt{\tau_1} + b_2\sqrt{\tau_2} + b_3\sqrt{\tau_3}} \quad (4)$$

Here, it is assumed that the composition and thickness of the metal film on the front side are all the same as those on the backside.

Further, when
$\tau_1 = \tau_3 = \tau_m$, $b_1 = b_3 = b_m$ and $R_{12} = R_{23} = R$ and if $\beta$, $\chi$ and $\rho$ are defined as follows, $$\beta = b_n/b_m, \chi = \sqrt{\tau_n}/\sqrt{\tau_m}, \rho = \frac{Rb_m}{\tau_m^{1/2}}$$

it is allowed to obtain the following equation.

$$A_{3b} = \frac{\left(\frac{4}{3}+\chi^2\right)+\beta\chi\left(1+\frac{\chi^2}{6}\right)+\frac{\chi}{\beta}+2(1+\beta\chi)\rho}{2+\beta\chi} \cdot \tau_m \quad (5)$$

In equation (5), when $\chi=0$, the following equation can be obtained.

$$A_{3b} = \left(\frac{2}{3}+\rho\right)\cdot\tau_m \quad (6)$$

When $\chi \to \infty$, the following equation can be obtained.

$$A_{3b} = \frac{\tau_n}{6} \quad (7)$$

When $\beta=1$, the following equation can be obtained.

$$A_{3b} = \left[\frac{(2+\chi)^2}{6}+\frac{2(1+\chi)}{2+\chi}\rho\right]\cdot\tau_m \quad (8)$$

Furthermore, a parameter represented by the following equation $$\chi=\sqrt{\tau_n}/\sqrt{\tau_m} \quad (9)$$

will vary in proportion to the thickness of a non-metal film. FIG. 3 is a graph which can be used to indicate how the areal heat diffusion time changes when $\beta$ and $\rho$ are used as parameters and $\chi$ is changed. It is understood that the value of $\rho$ can be evaluated from an area where $\chi$ value is small and that an interface thermal resistance can be calculated. On the other hand, in an area where $\chi$ value is large, areal heat diffusion time is no longer dependent on $\tau$, if the thermal diffusivity and the thermal effusivity of the respective metal films as well as the thickness of each film layer are known, it is possible to evaluate a thermal diffusivity of a non-metal film.

As described in the above, it is understood that using temperature change curves obtained when using the backside heating/front side temperature measuring type picosecond thermoreflectance method to measure the three-layer film structure associated with interface thermal resistance, it is possible to separately calculate the thermal diffusivity of the non-metal film as well as the thermal resistance on interfaces between the metal films and the non-metal film, and such a calculation may be carried out by using a response function method.

In this way, with the use of the present invention, even if a substance to be measured is a non-metal substance, providing a metal layer on ether side of the non-metal substance makes it possible to simultaneously measure thermal diffusivity and interface thermal resistances, by virtue of a picosecond thermoreflectance method.

Further, according to the method for measuring a thermal diffusivity within a three-layer substance, a plurality of substances (which are different from one another only in their thickness and their thermophysical properties are unknown) are prepared, both sides of each of the substances are formed with other layers which belong to the same sort of substance and are in the same state and have the predetermined known thermophysical properties, thereby carrying out the above measurement on each of the three-layer substances. Therefore, by using the same picosecond thermoreflectance method to measure the respective three-layer substances and analyzing the measured data, it is possible to correctly measure the thermal diffusivity within each of the three-layer film structures.

Moreover, according to the method for measuring a thermal diffusivity within a three-layer substance, by calculating an area defined by a transient temperature history curve on the backside of the pulse-heated three-layer substance and also by the horizontal axis corresponding to a pulse-heating time, it is possible to simultaneously measure thermal diffusivity of the three-layer substance as well as interface thermal resistances. Therefore, it is possible to use a response function method to correctly measure the thermal diffusivity within each three-layer film structure.

What is claimed is:

1. A method for measuring a thermal diffusivity and interface thermal resistances of a three-layer substance including a middle layer whose thermophysical properties are unknown, and two other layers formed on both side of the middle layer, said two other layers belonging to the same sort of substance and having known thermal properties, comprising:

heating by a pulse light one side of the three-layer substance;

observing at the same time a transitive temperature rising on the opposite side of the three-layer substance; and calculating an area defined by a transient temperature history curve on a backside of the pulse-heated three-layer substance and a horizontal axis corresponding to a pulse-heating time, thereby simultaneously measuring the thermal diffusivity within the three-layer substance and the interface thermal resistance.

2. The method according to claim 1, further comprising:

preparing a plurality of substances which are different from one another only in their thicknesses and whose thermophysical properties are unknown;

forming on both sides of each of the substances other substance layers which are in the same identical state and whose thermophysical properties are known; and measuring the thermal diffusivity and the interface thermal resistance of each of the three-layer substances.

* * * * *